United States Patent [19]

Drent

[11] Patent Number: 5,101,077
[45] Date of Patent: Mar. 31, 1992

[54] PROCESS FOR THE PREPARATION OF CARBONYL COMPOUNDS

[75] Inventor: Eit Drent, Amsterdam, Netherlands

[73] Assignee: Shell Oil Company, Houston, Tex.

[21] Appl. No.: 668,844

[22] Filed: Mar. 13, 1991

[30] Foreign Application Priority Data

May 14, 1990 [GB] United Kingdom ............... 9010786

[51] Int. Cl.$^5$ .............................................. C07C 45/45
[52] U.S. Cl. .................................... 568/361; 568/322
[58] Field of Search ................... 568/361, 403, 322

[56] References Cited

U.S. PATENT DOCUMENTS 3,557,217  1/1971  Royston ........................... 568/410
4,117,016  9/1978  Hughes ............................ 260/593 R

FOREIGN PATENT DOCUMENTS 0009429  2/1980  European Pat. Off. ............ 568/410

OTHER PUBLICATIONS

Kelly et al., "New Lewis Acid Catalysts for the Diels-Alder Reaction", Tetrahedron Letters, vol. 30, No. 111, pp. 1357–1360, 1989.

*Primary Examiner*—James H. Reamer

[57] ABSTRACT

A process is provided for the preparation of unsaturated carbonyl compounds having at least one cycloalkenic moiety in the molecule, which comprises contacting an allylic type unsaturated alcohol and a conjugated diene in the presence of a catalyst system obtainable by combining a Group VIII metal compound and a ligand containing one or more donor atoms selected from Group V A and VI A elements.

17 Claims, No Drawings

PROCESS FOR THE PREPARATION OF CARBONYL COMPOUNDS

FIELD OF THE INVENTION

The invention relates to a process for the preparation of unsaturated carbonyl compounds, and in particular to the preparation of unsaturated carbonyl compounds containing at least one cycloalkenic moiety in the molecule, and to the use of the thus prepared carbonyl compounds.

BACKGROUND OF THE INVENTION

Unsaturated carbonyl compounds such as unsaturated aldehydes and ketones are versatile and valuable compounds. Unsaturated monoaldehydes for example, are known to be used in the preparation of fragrances, while unsaturated ketones such as acetylcyclohexene, i.e. an unsaturated ketone wherein the carbonyl group is attached directly to a cycloalkenic group, are known to be used e.g. for the simultaneous preparation of adipic acid and acetic acid.

The preparation of unsaturated carbonyl compounds containing at least a cycloalkenic moiety in the molecule as described hereinbefore, is known e.g. from Tetrahedron Letters, Vol. 30, No. 11, pp 1357–1360, 1989. Said preparation relates to the Diels-Alder reaction of unsaturated carbonyl compounds and conjugated dienes in the presence of a Lewis acid catalyst such as catechol boron bromide. Although a wide range of such unsaturated carbonyl compounds is described, which compounds were generally prepared in a relatively high yield, the preparation described has a disadvantage in that the process uses already relatively expensive starting materials, and/or materials which are not always readily available, i.e. unsaturated carbonyl compounds. In U.S. Pat. No. 3,557,217 a process is described for the preparation of unsaturated carbonyl compounds, as described hereinbefore, which proceeds via the reaction of methyl vinyl ketone and a conjugated diene, the methyl vinyl ketone being a component of a by-product carbonyl stream from a process for the production of 1,3-butadiene, and in which stream acetone, methyl ethyl ketone, vinylcyclohexene, ethylbenzene, styrene and water are also present. Although this process uses a relatively cheap starting material, it is restricted to the production of unsaturated carbonyl compounds based on methyl vinyl ketone. Hence, it can be concluded that there is considerable need for improvement in the preparation of unsaturated carbonyl compounds as described hereinbefore.

The problem underlying the present invention is developing a process for the preparation of unsaturated carbonyl compounds, having at least a cycloalkenic moiety in the molecule, and which process does not have one of more of the disadvantages as mentioned hereinbefore.

As a result of extensive research and experimentation a process was developed for the preparation of unsaturated carbonyl compounds, of the type as described hereinbefore, by reaction of an allylic alcohol and a conjugated diene via the in situ formation of an unsaturated carbonyl compound. This process has the advantage in that it not only overcomes a separate preparation and isolation of the unsaturated carbonyl compound as employed in the process described in Tetrahedron Letters, Vol. 30, No. 11, pp 1357–1360, 1989, but moreover enables the preparation of a much wider range of the desired carbonyl compounds than would be possible according to the process as described in U.S. Pat. No. 3,557,217.

SUMMARY OF THE INVENTION

The invention thus provides a process for the preparation of unsaturated carbonyl compounds having at least one cycloalkenic moiety in the molecule, which comprises contacting an allylic-type unsaturated alcohol and a conjugated diene in the presence of a catalyst system comprising a Group VIII metal compound and a ligand containing one or more donor atoms selected from Group V A and VI A elements.

When in the context of the present invention reference is made to an element or metal of a group of the Periodic Table of the Elements, said group number refers to a group of the CAS version of the Periodic Table as published in the 68th Edition of the Handbook of Chemistry and Physics, CRC Press, Inc.

DESCRIPTION OF THE PREFERRED EMBODIMENTS

Suitable allylic alcohols for use in the process of the present invention include both primary and secondary allylic-type alcohols containing one or more allylic alcohol moieties, such as for example, allyl alcohol, 2-buten-1-ol, 3-buten-2-ol, 2-penten-1-ol, 3-penten-2-ol, 4-penten-3-ol, 3-methyl-3-buten-2-ol, 3-methyl-2-buten-1-ol, 2-methyl-7-butyl-4-tridecen-6-ol, 11-eicosen-10-ol, 2-cyclopenten-1-ol and 2-cyclohexen-1-ol. Other suitable allylic-type alcohols include substituted or modified allylic alcohols, such as for example, derivatives of the allylic alcohols as described hereinbefore, provided the substituents or modifications present therein do not interfere with the preparation of the desired product, such as for example, ether and hydroxyl groups as well as the hereinbefore exemplified alkyl substituents.

Conjugated dienes which may be used in the process of the present invention include both acyclic and cyclic conjugated diene compounds. Preferred acyclic conjugated dienes will have from 4–10 carbon atoms and include 1,3-butadiene, isoprene, 1,3-pentadiene, 1,3-hexadiene and 2,4-hexadiene. Examples of cyclic conjugated dienes include 1,3-cyclopentadiene and 1,3-cyclohexadiene. Further suitable acyclic and cyclic conjugated dienes for use in the present process include substituted or modified conjugated dienes, such as modifications of conjugated dienes as mentioned hereinbefore, provided the modifications do not affect the preparation of the desired compound. Examples of such modified conjugated dienes include those containing more than the two olefinically unsaturated entities of the diene moiety, such as for example, 3-methyl-1,4,6-heptadiene and 7-methyl-3-methylene-1,6-octadiene; alkyl-substituted conjugated dienes such as 2,3-dimethyl-1,3-butadiene, 1,1,2-trimethyl-1,3-cyclopentadiene and 1,3,5,5-tetramethyl-1,3-cyclohexadiene; and halogenated conjugated dienes such as chloroprene.

As mentioned hereinbefore, the process of the present invention is conducted in the presence of a catalyst system obtainable by contacting a Group VIII metal compound and a ligand. Suitable Group VIII metal compounds include Group VIII metal oxides, salts such as halides, sulfates, sulfonates such as p-toluenesulfonates, methanesulfonates and trifluoromethanesulfonates, nitrates, nitrites, phosphates, phosphonates, carboxylates, substituted carboxylates such as halogenated carboxylates and exemplified by trifluoroacetate, as well as acetylacetonates and complexes of Group VIII metals such as Group VIII metal phosphine complexes.

Preferred Group VIII metal compounds for the catalyst system for use in the process of the present invention are based on a non- or weakly-coordinating anion, which anions are generally based on acids having a $pk_a < 3.0$ (measured in water at 25° C.) and more preferably a $pk_a < 2.0$. Preferred such acids include sulfonic acids such as p-toluenesulfonic acid, methanesulfonic acid and trifluoromethanesulfonic acid and halogenated carboxylic acids such a trifluoroacetic acid.

Preferred Group VIII metals compounds, as described hereinbefore, are ruthenium, irridium, rhodium and iron compounds, and more preferably ruthenium compounds.

The ligand as defined hereinbefore with which the Group VIII metal compound is combined to obtain the hereinabove mentioned catalyst system may conveniently include.

1) compounds of the general formula

(I)

wherein X and Y represent similar or different organic bridging groups, each having three or four atoms in the bridge at least two of which are carbon atoms, such as 2,2'-bipyridine and derivatives thereof, such as 4,4'-dimethyl-2,2'-bipyridine, 4,4'-dichloro-2,2'-bipyridine, 4,4'-dimethoxy-2,2'-bipyridine, 2,2'-(3,6-dithiaoctamethylene) dipyridine, and 4,4'-dicarboxy-2,2'-bipyridine; 1,10-phenanthroline and derivatives thereof, such as 5-chloro-1,10-phenanthroline, 4,7-diphenyl-1,10-phenanthroline, 4,7-dimethyl-1,10-phenanthroline, 2,9-dichloro-1,10-phenanthroline, 5,6-dimethyl-1,10-phenanthroline, 1,10-phenanthroline-5-sulfonic acid, 4,7-diphenyl-1,10 phenanthroline disulfonic acid and 4,7-dimethyl-1,10-phenanthroline disulfonic acid sodium; 2,2'-biquinoline, 2-(2-pyridyl)benzimidazole, 3-(2-pyridyl)-5,6-diphenyl-1,2,4-triazine and 3-(2-pyridyl)-5,6-diphenyl-1,2,4-triazine-p,p'-disulfonic acid sodium, 2) compounds in which one phosphorus atom and one or more nitrogen atoms, which atoms bear no hydrogen, are present, and in which each one of the nitrogen atoms is connected to the phosphorus atom via an organic bridging group having at least one carbon atom in the bridge, such as 2-cyanoethyl-diphenylphosphine, tris(2-cyanoethyl)phosphine, 2-pyridyl-diphenylphosphine, bis(2-pyridyl)-phenylphosphine, and 3-(diphenyl-phosphino)-N,N-dimethyl-propion amide, 3) compounds of the general formula $R_1R_2M_1$-$R$-$M_2R_3R_4$, wherein $M_1$ is arsenic or antimony, $M_2$ is an element with an atomic number lower than that of $M_1$ and chosen from the group made up of arsenic, phosphorus and nitrogen, $R_1$, $R_2$, $R_3$ and $R_4$ represent similar or different hydrocarbon groups which may or may not be substituted with polar groups and R represents a bivalent bridging group having 2–4 atoms in the bridge, such as 1-(diphenylphosphino)-3-(diphenylarsino) propane, 1-(diphenylphosphino)-3-(diphenylstibino) propane, 1-(diphenylarsino)-3-(dimethylamino) propane, and 1-(diphenylphosphino)-2-(diphenylarsino) ethane, 4) compounds of the general formula $R_1R_2M$-$R$-$MR_3R_4$, wherein M is an element chosen from the group made up of phosphorus, arsenic and antimony, and wherein $R_1$, $R_2$, $R_3$ and $R_4$ and R have the meanings given hereinbefore, such as 1,3-bis(diphenylarsino) propane, 1,3-bis(diphenylphosphino) propane, 1,4-bis(diphenylphosphino) butane, 1,2-bis(diphenylphosphino) ethane, 1,3-bis[di(4-methoxyphenyl) phosphino] propane, 2-methyl-2-(diphenylphosphinomethyl)-1,3-bis(diphenylphosphino) propane and $N,N,N^1,N^1$-tetrakis(diphenylphosphinomethyl) ethylenediamine, 5) compounds of general formula $R^1M^1$-$R$-$M^2$-$R^3$, wherein $M^1$ and $M^2$ are similar or different elements chosen from the group consisting of sulfur, selenium and tellurium, $R^1$ and $R^2$ are similar or different, optionally polar-substituted, hydrocarbon groups and R represents a bivalent bridging group containing at least two carbon atoms in the bridge, or $R^1$ and $M^1$ and/or $R^2$ and $M^2$ form a heterocyclic ring with a carbon atom of the bridging group R. Preferred ligands for use in the process of the present invention are bidentate ligands and especially preferred are bidentate ligands of general formula I such as the 2,2'-bipyridines and 1,10-phenanthrolines.

The ligand component will generally be employed in an amount which corresponds with a ratio in the range of from about 0.25 to about 10 moles of ligand per gram atom of Group VIII metal and preferably in the range of from about 0.5 to about 5.

Although not being an essential feature of the process of the present invention, the ligand on which the catalyst system is based may conveniently be an immobilized or a supported ligand, i.e. a ligand which has been anchored to a supporting material such as for example a silica, an alumina or a polymeric material. Ligands anchored to a supporting material are known. The use of such a ligand may be advantageous when catalyst retrieval or removal is an important aspect, or e.g. in the event of a continuous reaction procedure.

In view of the preference expressed hereinbefore for catalyst systems obtained by combining a Group VIII metal compound based on a non- or weakly-coordinating anion, i.e. an anion of an acid having a $pk_a < 3.0$ (as measured in water at 25° C.) and a ligand, it is also possible to generate such a Group VIII metal compound by contacting a Group VIII metal compound not based on an anion of an acid having a $pk_a < 3$, with an acid having a $pk_a < 3.0$. Acids having a $pk_a < 3$ as defined hereinbefore may be selected from a wide range of organic and inorganic acids such as, for example, halogenated carboxylic acids, sulfonic acids, halogenated sulfonic acids, phosphonic acids, hydrohalogenic acids, orthophosphonic acid, pyrophosphonic acid and fluorosilicic acids. Preferred such acids have a $pk_a < 2.0$ and may be selected from the group consisting of p-toluenesulfonic acid, trifluorocarboxylic acids, methanesulfonic acid, trifluorosulfonic acid, sulfuric acid and perchloric acid.

The process of the present invention may conveniently be conducted by contacting the allylic alcohol, the conjugated diene, a Group VIII metal compound and a ligand, in a suitable reactor at a temperature in the range of from about 60° C. to about 220° C. and preferably in the range of from about 100° C. to about 170° C. and under autogenic pressure. When following the procedure of in situ generating a Group VIII metal compound based on a non-or weakly-coordinating anion, the reaction medium may also include a sufficient amount of an acid having a $pk_a < 3$, as defined hereinbefore.

The amount of catalyst used with respect to the reactant is not critical and will generally correspond with a range of from about $10^{-7}$ to about $10^{-1}$ gram atom of Group VIII metal per mole of allylic alcohol, and more particularly in the range of from $10^{-5}$-$10^{-2}$ gram atom of metal per mole of allylic alcohol converted to desired product.

In the process of the present invention, the molar ration of conjugated diene and allylic alcohol may very over wide ranges but is preferably at least about 2:1. When employing a lower molar ratio the amount of diene can be a limiting factor for the allylic alocohol conversion.

Although the process of the present invention may be conducted as described hereinbefore, i.e. with a reaction medium essentially comprising an allylic alcohol, a conjugated diene and any reaction product formed, it may be advantageous to conduct said process in the presence of a solvent compound. Compounds which may be employed as solvent include hydrocarbon compounds, such as, for example, n-decane, as well as more polar solvents such as the dimethyl ether of diethylene glycol and the corresponding higher homologues. Water may also be present in the reaction medium.

The process of the present invention offers the possibility to prepare a wide range of unsaturated carbonyl compounds having at least one cycloalkenic moiety in the molecule. More particular, the unsaturated carbonyl compounds which may be prepared according to the process of the present invention will have the carbonyl group attached directly to a hydrocarbyl ringstructure comprising at least one cycloalkenic moiety, as well being attached to a hydrogen or carbon atom, or alternatively the carbon atom of the carbonyl group forms part of said hydrocarbyl ringstructure. Carbonyl compounds wherein the carbonyl group is also directly attached to a hydrogen atom, will be based on allylic alcohols having a primary hydroxyl group, whereas those having the carbonyl group not attached to a hydrogen atom will be based on allylic alcohols having a secondary hydroxyl group.

Carbonyl compounds having the carbonyl group attached to a hydrocarbyl ringstructure as described hereinbefore and wherein said ringstructure is an optionally substituted cyclohexenyl group will be obtainable from the combination of an acyclic conjugated diene and an acyclic allylic alcohol. With the carbonyl compounds obtainable from the combination of a cyclic conjugated diene such as 1,3-cyclopentadiene or 1,3-cyclohexadiene and an acyclic allylic alcohol, the hydrocarbyl ringstructure will be respectively an optionally substituted 2-norbornene or bicyclo[2,2,2]oct-2-ene group. With carbonyl compounds obtained from the combination of a cyclic allylic alcohol, such as, for example, an optionally substituted 2-cyclohexen-1-ol, and an acyclic conjugated diene, the carbonyl compound will be an optionally substituted 2-oxo-bicyclo[4.4.0]dec-7-ene compound.

The unsaturated carbonyl compounds prepared according to the process of the present invention may conveniently be isolated from the reaction mixture by known techniques such as distillation or extraction.

The unsaturated carbonyl compounds which may be prepared according to the process of the present invention are potentially suitable for the preparation of e.g. fine chemicals and fragrances.

The invention will be further illustrated with the following examples for which the following information is provided. These examples are intended for purposes of illustration and are not to be construed as limitations on the scope of the present invention.

Abbreviations
acac: acatylacetonate
Diglyme: dimethyl ether of diethylene glycol
MCK: methyl cyclohexenyl ketone
MEK: methyl ethyl ketone

EXAMPLES 1-3

The appropriate amount of 3-buten-2-ol, diglyme, water, group VIII metal compound, 1,10-phenanthroline and paratoluenesulfonic acid (PTSA) were introduced into a 250 ml stainless steel (Hastelloy C) autoclave. Subsequently the reactor was closed and the air evacuated, whereupon the appropriate amount of 1,3-butadiene was pumped in, which was followed by heating the reactor contents for 5 hours at the desired temperature under autogenic pressure. At the end of the reaction period the reactor contents were cooled to approximately 20° C. and analysed by gas liquid chromatography. The relevant analytical data have been collected in Table I, which Table also presents the type and amount of the compounds used as well as the reaction temperature.

TABLE I

|  |  | Example | | |
|---|---|---|---|---|
|  |  | 1 | 2 | 3 |
| Ru(acac)$_3$ | mmol | 0.5 | 0.5 | — |
| NaIrCl$_6$ | " | — | — | 0.5 |
| 1,10-Phenanthroline | " | 0.5 | 0.5 | 1 |
| PTSA | " | 1.5 | 1.5 | 7 |
| Diglyme | ml | 40 | 45 | 40 |
| Water | " | — | 10 | 10 |
| 3-buten-2-ol | " | 5 | 10* | 10 |
| 1,3-butadiene | " | 20 | 10 | 10 |
| Temp. | °C. | 130 | 140 | 130 |
| MCK | %** | 70 | 30 | 20 |
| MEK | " | ~30 | 40 | — |

*g
**based on alcohol conversion

What is claimed is:

1. A process for the preparation of unsaturated carbonyl compounds having at least one cycloalkenic moiety in the molecule, which comprises contacting an allylic-type unsaturated alcohol and a conjugated diene in the presence of a catalyst system comprising a Group VIII metal compound based on a metal selected from the group consisting of ruthenium, irridium, rhodium, iron and mixtures thereof, and a ligand having a general formula

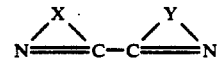

wherein X and Y represent similar or different organic bridging groups each having three or four atoms in the bridge at least two of which are carbon atoms.

2. The process of claim 1, wherein the group VIII metal compound is based on a non- or weakly-coordinating anion.

3. The process of claim 2, wherein the anion is based on an acid having a pk$_a$<3 (as measured in water at 25° C.).

4. The process of claim 3, wherein the acid has a pk$_a$<2 (as measured in water at 25° C.).

5. The process of claim 1, wherein the Group VIII metal is ruthenium.

6. The process of claim 1, wherein the ligand is a bidentate ligand.

7. The process of claim 1, wherein the ligand is selected from the group consisting of 1,10-phenanthrolines and 2,2'-bipyridines.

8. The process of claim 1, wherein the ligand is present in an amount which corresponds with a ratio in the range of from 0.25-10 moles of ligand per gram atom of Group VIII metal.

9. The process of claim 8, wherein the ratio of moles of ligand per gram atom of Group VIII metal is in the range of from from 0.5 to about 5.

10. The process of claim 1, wherein the amount of catalyst employed corresponds with a range of from about $10^{-7}$ to about $10^{-1}$ gram atom of Group VIII metal per mole of allylic-type alcohol converted to desired product.

11. The process of claim 10, wherein the amount of catalyst corresponds with a range of from about $10^{-5}$ to about $10^{-2}$ gram atom of Group VIII metal per mole of allylic-type alcohol.

12. The process of claim 1, wherein said process is conducted at a temperature in the range of from about 60° C. to about 220° C.

13. The process of claim 12, wherein the temperature is in the range of from about 100° C. to about 170° C.

14. The process of claim 1, wherein the reaction medium includes a solvent.

15. The process of claim 1, wherein an acyclic conjugated diene and an acyclic allylic alcohol is employed.

16. The process of claim 1, wherein a cyclic conjugated diene and an acyclic allylic alcohol is employed.

17. The process of claim 1, wherein an acyclic conjugated diene and a cyclic allylic alcohol is employed.

* * * * *